(12) United States Patent
Schmitt et al.

(10) Patent No.: US 9,320,799 B2
(45) Date of Patent: Apr. 26, 2016

(54) ESTERIFIED CELLULOSE ETHERS HAVING A SPECIFIC SUBSTITUENT DISTRIBUTION

(71) Applicant: Dow Global Technologies LLC, Midland, MI (US)

(72) Inventors: Robert L. Schmitt, Annandale, NJ (US); Robert L. Sammler, Midland, MI (US); Meinolf Brackhagen, Walsrode (DE); Oliver Petermann, Hamburg (DE); Roland Adden, Walsrode (DE); Nicholas S. Grasman, Midland, MI (US); Steven J. Guillaudeu, Midland, MI (US)

(73) Assignee: Dow Global Technologies LLC

( * ) Notice: Subject to any disclaimer, the term of this patent is extended or adjusted under 35 U.S.C. 154(b) by 0 days.

(21) Appl. No.: 14/390,041

(22) PCT Filed: Oct. 24, 2012

(86) PCT No.: PCT/US2012/061586
§ 371 (c)(1),
(2) Date: Oct. 2, 2014

(87) PCT Pub. No.: WO2013/154607
PCT Pub. Date: Oct. 17, 2013

(65) Prior Publication Data
US 2015/0065547 A1    Mar. 5, 2015

Related U.S. Application Data

(60) Provisional application No. 61/622,754, filed on Apr. 11, 2012.

(51) Int. Cl.
| | |
|---|---|
| *A61K 31/343* | (2006.01) |
| *A61K 31/4166* | (2006.01) |
| *A61K 47/10* | (2006.01) |
| *A61K 47/38* | (2006.01) |
| *A61K 9/14* | (2006.01) |
| *A61K 9/48* | (2006.01) |
| *C08B 13/00* | (2006.01) |
| *C08B 11/193* | (2006.01) |
| *A61K 9/08* | (2006.01) |

(52) U.S. Cl.
CPC . *A61K 47/38* (2013.01); *A61K 9/08* (2013.01); *A61K 9/145* (2013.01); *A61K 9/146* (2013.01); *A61K 9/4816* (2013.01); *A61K 9/4858* (2013.01); *A61K 9/4866* (2013.01); *A61K 31/343* (2013.01); *A61K 31/4166* (2013.01); *A61K 47/10* (2013.01); *C08B 11/193* (2013.01); *C08B 13/00* (2013.01)

(58) Field of Classification Search
None
See application file for complete search history.

(56) References Cited

U.S. PATENT DOCUMENTS

| | | | |
|---|---|---|---|
| 3,435,027 A | 3/1969 | Desmarais et al. | |
| 4,226,981 A | 10/1980 | Onda et al. | |
| 4,316,982 A | 2/1982 | Holst et al. | |
| 4,365,060 A | 12/1982 | Onda et al. | |
| 5,756,036 A * | 5/1998 | Grosswald et al. | 264/304 |

FOREIGN PATENT DOCUMENTS

| | | |
|---|---|---|
| EP | 0210917 A2 | 2/1987 |
| EP | 1141029 B1 | 5/2003 |
| EP | 1423433 B1 | 3/2007 |
| WO | 2005115330 A2 | 12/2005 |
| WO | 2011159626 A1 | 12/2011 |

OTHER PUBLICATIONS

Adden, Cellulose (2006) 13:459-476.*
Mol. Pharma., 2011, vol. 8, p. 564-570, Excipient-Mediated Supersaturation Stabilization in Human Intestinal Fluids, Bevernage et al.
Pharm. Research, 2009, vol. 26, No. 6,Utility of Hydroxypropylmethylcellulose Acetate Succinate, Curatolo et al.
Mol.Pharma., 2008, vol. 5, No. 6, p. 1003-1019, Hydroxypropyl Methylcellulose Acetate Succinate-Based Spray-Dried Dispersions: An Overview, Friesen et al.
J. Chem. Inf.Comput. Sci., 1987, 27, p. 21-35, Atomic Physicochemical Parameters for Three-Dimensional-Structure-Directed Quantitative Structure-Activity Relationships, Ghose et al.
J. Chem. Inf.Comput.Sci, 1989, 29, p. 163-172, Atomic Physicochemical Parameters for Three Dimensional Structure Directed Quantitative Structure-Activity Relationships, Viswanadhan et al.
Eur. J.Med.Chem. Chim., 1984, 19, No. 1, p. 71-78, Molecular structures, Broto et al.

* cited by examiner

*Primary Examiner* — Layla Berry

(57) ABSTRACT

An esterified cellulose ether comprises (i) aliphatic monovalent acyl groups or (ii) groups of the formula —C(O)—R—COOA wherein R is a divalent aliphatic or aromatic hydrocarbon group and A is hydrogen or a cation or (iii) a combination of aliphatic monovalent acyl groups and groups of the formula —C(O)—R—COOA, wherein the cellulose ether has anhydroglucose units joined by 1-4 linkages and has methyl groups, hydroxyalkyl groups, and optionally alkyl groups being different from methyl as substituents such that the esterified cellulose ether has an MS (hydroxyalkyl) of 0.05 to 1.00, and hydroxyl groups of anhydroglucose units are substituted with methyl groups such that [s23/s26−0.2*MS (hydroxyalkyl)] is 0.36 or less, wherein s23 is the molar fraction of anhydroglucose units wherein only the two hydroxyl groups in the 2- and 3-positions of the anhydroglucose unit are substituted with a methyl group and wherein s26 is the molar fraction of anhydroglucose units wherein only the two hydroxyl groups in the 2- and 6-positions of the anhydroglucose unit are substituted with a methyl group. The esterified cellulose ether is useful as an excipient for poorly water-soluble drugs.

15 Claims, 1 Drawing Sheet

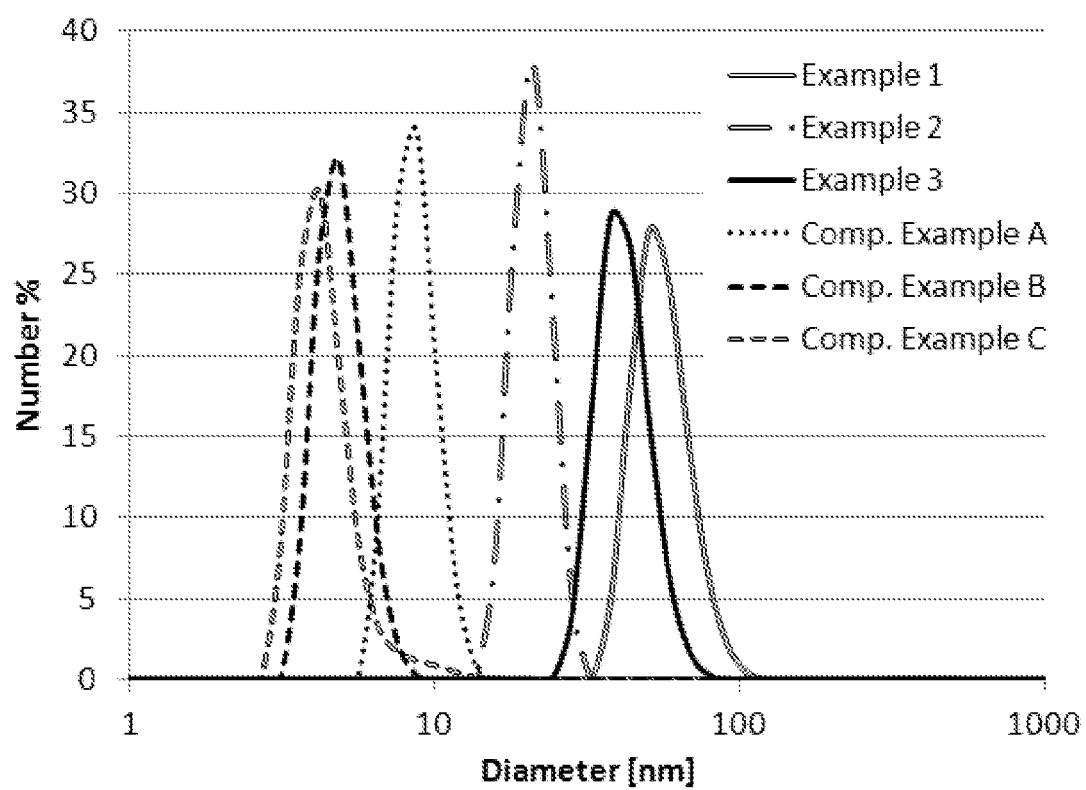

ESTERIFIED CELLULOSE ETHERS HAVING A SPECIFIC SUBSTITUENT DISTRIBUTION

FIELD

This invention concerns esterified cellulose ethers, a process for preparing them, a liquid composition comprising an organic diluent and an esterified cellulose ether, a process for coating a dosage form and for manufacturing capsules using the liquid composition and a solid dispersion of an active ingredient in the esterified cellulose ether.

INTRODUCTION

Esters of cellulose ethers, their uses and processes for preparing them are generally known in the art. One process for producing cellulose ether-esters is described in U.S. Pat. No. 3,435,027.

U.S. Pat. No. 4,365,060 discloses enterosoluble capsules which are said to have excellent enterosolubility behavior as well as a sufficient pliability even without the addition of a plasticizer.

A large number of presently known drugs have a low solubility in water, so that complex techniques are required to prepare a dosage form. One known method includes dissolving such drug together with a pharmaceutically acceptable water-soluble polymer in an organic solvent that is optionally blended with water, and to spray-dry the solution. The pharmaceutically acceptable water-soluble polymer is aimed at reducing the crystallinity of the drug, thereby minimizing the activation energy necessary for the dissolution of the drug, as well as establishing hydrophilic conditions around the drug molecules, thereby improving the solubility of the drug itself to increase its bioavailability, i.e., its in vivo absorption by an individual upon ingestion.

International Patent Application WO 2005/115330 discloses hydroxypropyl methyl cellulose acetate (HPMCA) polymers and hydroxypropyl methyl cellulose acetate succinate (HPMCAS) polymers with a specific combination of substitution levels. The HPMCA polymer has a degree of substitution of acetyl groups ($DOS_{Ac}$) of at least 0.15. The HPMCAS polymer has a degree of substitution of succinoyl groups ($DOS_S$) of at least 0.02, a $DOS_{Ac}$ of at least 0.65 and a sum of $DOS_{Ac}$ and $DOS_S$ of at least 0.85. WO 2005/115330 discloses that these HPMCAS and HPMCA polymers are useful for forming solid amorphous dispersions of hydrophobic drugs and suggests that when these HPMCAS and HPMCA polymers are used in combination with drugs that are prone to rapid crystallization from supersaturated aqueous solutions, the HPMCAS and HPMCA polymers are particularly effective at sustaining high drug concentrations and thereby enhancing absorption of drug in vivo. WO 2005/115330 discloses that the increased acetate substitution allows increased solubility of active agents in spray-dried solutions, while the increased succinate substitution increases the solubility of the polymer in aqueous solution.

International Patent Application WO 2011/159626 discloses an active ingredient and HPMC-AS having a degree of substitution of methoxy groups ($DS_M$) of ≤1.45, and a combined degree of substitution of acetyl groups ($DS_{Ac}$) and succinoyl groups ($DS_s$) of ($DS_{Ac}+DS_s$)≥1.25.

However, in view of the large diversity of drugs, it is self-evident that a limited variety of esterified cellulose ethers, such as HPMCAS and HPMCA, cannot fulfill all needs. Accordingly, it is an object of the present invention to find new esterified cellulose ethers, such as new grades of HPMCAS and HPMCA, to enrich the variety of polymers which are useful as excipients of poorly water-soluble drugs. It is a preferred object of the present invention to find new esterified cellulose ethers, such as new grades of HPMCAS and HPMCA, which increase the solubility of active agents in spray-dried solutions in another manner than increasing the acetate substitution. For example, the use of HPMCAS of a high ratio of acetate/succinate substitution increases the pH at which the HPMCAS is soluble in aqueous solutions, which decreases their usefulness for increasing the bioavailability of drugs in certain biological systems, such as the upper part of the intestine of the human body. In general the dissolution of HPMCAS of a high ratio of acetate/succinate substitution only occurs in the lower part of the intestine of the human body which reduces the time for absorption and therefore bioavailability in the intestine.

SUMMARY

One aspect of the present invention is an esterified cellulose ether comprising (i) aliphatic monovalent acyl groups or (ii) groups of the formula —C(O)—R—COOA wherein R is a divalent aliphatic or aromatic hydrocarbon group and A is hydrogen or a cation or (iii) a combination of aliphatic monovalent acyl groups and groups of the formula —C(O)—R—COOA, wherein the esterified cellulose ether has anhydroglucose units joined by 1-4 linkages and has methyl groups, hydroxyalkyl groups, and optionally alkyl groups being different from methyl as substituents such that the esterified cellulose ether has an MS (hydroxyalkyl) of 0.05 to 1.00,
and
hydroxyl groups of anhydroglucose units are substituted with methyl groups such that [s23/s26−0.2*MS(hydroxyalkyl)] is 0.36 or less,
wherein s23 is the molar fraction of anhydroglucose units wherein only the two hydroxyl groups in the 2- and 3-positions of the anhydroglucose unit are substituted with a methyl group and
wherein s26 is the molar fraction of anhydroglucose units wherein only the two hydroxyl groups in the 2- and 6-positions of the anhydroglucose unit are substituted with a methyl group.

Another aspect of the present invention is a process for preparing the esterified cellulose ether described above, which process comprises the step of reacting a cellulose ether with (i) an aliphatic monocarboxylic acid anhydride or (ii) a dicarboxylic acid anhydride or (iii) a combination of an aliphatic monocarboxylic acid anhydride and a dicarboxylic acid anhydride, wherein
the cellulose ether has anhydroglucose units joined by 1-4 linkages and has methyl groups, hydroxyalkyl groups, and optionally alkyl groups being different from methyl as substituents such that
the cellulose ether has an MS (hydroxyalkyl) of 0.05 to 1.00, and
hydroxyl groups of anhydroglucose units are substituted with methyl groups such that [s23/s26−0.2*MS(hydroxyalkyl)] is 0.31 or less,
wherein s23 is the molar fraction of anhydroglucose units wherein only the two hydroxyl groups in the 2- and 3-positions of the anhydroglucose unit are substituted with a methyl group and
wherein s26 is the molar fraction of anhydroglucose units wherein only the two hydroxyl groups in the 2- and 6-positions of the anhydroglucose unit are substituted with a methyl group.

Yet another aspect of the present invention is a liquid composition which comprises an organic diluent and at least one esterified cellulose ether as described above.

Yet another aspect of the present invention is a liquid composition which comprises an aqueous diluent and at least one esterified cellulose ether as described above. Yet another aspect of the present invention is a process for coating a dosage form which comprises the step of contacting the above-mentioned liquid composition with the dosage form.

Yet another aspect of the present invention is a process for the manufacture of capsules which comprises the step of contacting the above-mentioned liquid composition with dipping pins.

Yet another aspect of the present invention is a solid dispersion of at least one active ingredient in at least one esterified cellulose ether as described above.

BRIEF DESCRIPTION OF DRAWINGS

FIG. 1 illustrates the colloid diameter of esterified cellulose ethers of the present invention and of comparative and known comparable esterified cellulose ethers.

DETAILED DESCRIPTION

The esterified cellulose ethers of the present invention and the cellulose ethers which are used as a starting material for producing the esterified cellulose ether have anhydroglucose units joined by 1-4 linkages and which has methyl groups, hydroxyalkyl groups, and optionally alkyl groups being different from methyl as substituents. The hydroxyalkyl groups can be the same or different from each other. Preferably the cellulose ether comprises one or two kinds of hydroxyalkyl groups, more preferably one or more kinds of hydroxy-$C_{1-3}$-alkyl groups, such as hydroxypropyl and/or hydroxyethyl. Useful optional alkyl groups are, e.g., ethyl or propyl, ethyl being preferred. Preferred ternary cellulose ethers are ethyl hydroxypropyl methyl celluloses, ethyl hydroxyethyl methyl celluloses, or hydroxyethyl hydroxypropyl methyl celluloses. Preferred cellulose ethers are hydroxyalkyl methyl celluloses, particularly hydroxy-$C_{1-3}$-alkyl methyl celluloses, such as hydroxypropyl methylcelluloses or hydroxyethyl methylcelluloses.

An essential feature of the esterified cellulose ethers of the present invention as described below and of the cellulose ethers which are used as starting materials for producing the esterified cellulose ethers is their unique distribution of methyl groups on the anhydroglucose units, expressed as [s23/s26−0.2*MS(hydroxyalkyl)]. As used herein, the symbol "*" represents the multiplication operator. Methods for determining [s23/s26−0.2*MS(hydroxyalkyl)] are described in more details in the Examples for hydroxypropyl methyl cellulose (HPMC) and hydroxypropyl methyl cellulose acetate succinate (HPMCAS). Based on the methods disclosed in the Examples, the skilled artisans know how to determine [s23/s26−0.2*MS(hydroxyalkyl)] of other cellulose ethers and esterified cellulose ethers.

In the esterified cellulose ethers of the present invention [s23/s26−0.2*MS(hydroxyalkyl)] is 0.36 or less, preferably 0.33 or less. In even more preferred embodiments of the invention the esterified cellulose ethers have an [s23/s26−0.2*MS(hydroxyalkyl)] of 0.31 or less, preferably 0.30 or less, more preferably 0.27 or less, most preferably 0.25 or less, and particularly 0.23 or less, or 0.21 or less, or even 0.19 or less.

In the cellulose ethers used as a starting material [s23/s26−0.2*MS(hydroxyalkyl)] is generally 0.31 or less, preferably 0.30 or less, more preferably 0.27 or less, most preferably 0.25 or less, and particularly 0.23 or less, or 0.21 or less, or even 0.19 or less.

In the esterified cellulose ethers of the present invention and in the cellulose ethers used as a starting material [s23/s26−0.2*MS(hydroxyalkyl)] is typically 0.07 or more, more typically 0.10 or more, and most typically 0.13 or more.

In the ratio s23/s26, s23 is the molar fraction of anhydroglucose units wherein only the two hydroxyl groups in the 2- and 3-positions of the anhydroglucose unit are substituted with methyl groups and s26 is the molar fraction of anhydroglucose units wherein only the two hydroxyl groups in the 2- and 6-positions of the anhydroglucose unit are substituted with methyl groups. For determining the s23, the term "the molar fraction of anhydroglucose units wherein only the two hydroxyl groups in the 2- and 3-positions of the anhydroglucose unit are substituted with methyl groups" means that the 6-positions are not substituted with methyl; for example, they can be unsubstituted hydroxyl groups or they can be substituted with hydroxyalkyl groups, methylated hydroxyalkyl groups, alkyl groups different from methyl or alkylated hydroxyalkyl groups or acyl groups. For determining the s26, the term "the molar fraction of anhydroglucose units wherein only the two hydroxyl groups in the 2- and 6-positions of the anhydroglucose unit are substituted with methyl groups" means that the 3-positions are not substituted with methyl; for example, they can be unsubstituted hydroxyl groups or they can be substituted with hydroxyalkyl groups, methylated hydroxyalkyl groups, alkyl groups different from methyl or alkylated hydroxyalkyl groups or acyl groups.

The term "hydroxyl group substituted with a methyl, hydroxyalkyl, an alkyl or acyl group" as used herein means that the hydrogen atom on the hydroxyl group is replaced by a methyl, hydroxyalkyl, an alkyl or acyl group.

Formula I below, wherein R1 is H, alkyl or acyl, illustrates the numbering of the hydroxyl groups in anhydroglucose units (AGU). Formula I is only used for illustrative purposes and does not represent the esterified cellulose ethers of the invention; the substitution with hydroxyalkyl groups is not shown in Formula I.

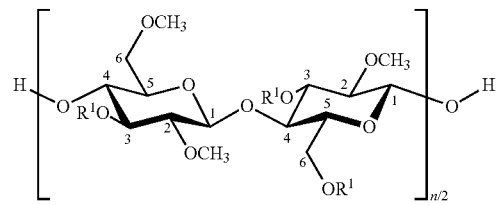

Formula I

The esterified cellulose ethers of the present invention and the cellulose ethers used as a starting material preferably have a DS(methyl) of from 1.0 to 2.5, more preferably from 1.1 to 2.4, most preferably from 1.2 to 2.2 and particularly from 1.6 to 2.05. The degree of the methyl substitution, DS(methyl), of a cellulose ether and of an esterified cellulose ether is the average number of OH groups substituted with methyl groups per anhydroglucose unit. For determining the DS(methyl), the term "OH groups substituted with methyl groups" does not only include the methylated OH groups directly bound to the carbon atoms of the cellulose backbone but also methylated OH groups that have been formed after hydroxyalkylation.

The esterified cellulose ethers of the present invention and the cellulose ethers used as a starting material have an MS(hydroxyalkyl) of 0.05 to 1.00, preferably 0.08 to 0.90, more preferably 0.12 to 0.70, most preferably 0.15 to 0.60, and particularly 0.20 to 0.50. The degree of the hydroxyalkyl substitution is described by the MS (molar substitution). The MS(hydroxyalkyl) is the average number of hydroxyalkyl groups which are bound by an ether bond per mole of anhydroglucose unit. During the hydroxyalkylation, multiple substitutions can result in side chains.

The sum of the MS(hydroxyalkyl) and the DS(methyl) preferably is at least 1.5, more preferably at least 1.9, and preferably up to 2.7, more preferably up to 2.5.

The determination of the % methoxyl and % hydroxypropoxyl in hydroxypropyl methylcellulose (HPMC) used as a starting material for producing an esterified HPMC is carried out according to the United States Pharmacopeia (USP 35). The % methoxyl and % hydroxypropoxyl of the esterified HPMC are determined in the same manner as described for "Hypromellose", United States Pharmacopeia and National Formulary, USP 35, pp 3467-3469. The values obtained as % methoxyl and % hydroxypropoxyl are subsequently converted into degree of substitution (DS) for methyl substituents and molar substitution (MS) for hydroxypropyl substituents. Residual amounts of salt are taken into account in the conversion. Based on these methods, the skilled artisans know how to determine MS(hydroxyalkyl) and DS(methyl) of other cellulose ethers and esterified cellulose ethers.

Methods of making the above described cellulose ethers are described in detail in the Examples. Some aspects of the process for making the cellulose ethers are described in more general terms below.

The cellulose ether described above can be obtained by a multistage etherification process comprising:

a first stage comprising:
  i. treating cellulose pulp with a first amount of alkalizing agent, and
  ii. addition of at least one methylating agent to the cellulose pulp, subsequent heating of the reaction mixture to a reaction temperature of 70° C. or more and thereafter at least one additional stage comprising:
  iii. addition of an additional amount of alkalizing agent to the reaction mixture at a rate of less than 0.055 molar equivalents of alkalizing agent per mole of anhydroglucose units per minute, and, optionally for each individual additional stage,
  iv. addition of an additional amount of at least one methylation agent to the reaction mixture, wherein before, after or concurrently with the addition of the alkalizing agent in the first stage at least one hydroxyalkylating agent, and optionally at least one alkylation agent different from a methylating agent, is added to the cellulose pulp, or, as the etherification of the cellulose pulp proceeds, to the partially reacted cellulose pulp.

The cellulose raw material for preparing the cellulose ether is typically cellulose pulp obtained from cotton or wood, preferably wood pulp. It is typically provided in powder or chip form.

In the above-mentioned process the cellulose pulp or, as the reaction of cellulose pulp to the hydroxyalkyl methyl cellulose proceeds, the partially reacted cellulose pulp, is alkalized in two or more stages, preferably in two or three stages, in one or more reactors with an alkalizing agent. The alkalizing agent may be any strong base such as an alkali metal hydroxide, preferably sodium hydroxide, caustic soda or lime or a mixture of more than one of such strong bases, employed as an aqueous solution. Usually an aqueous solution of an alkali metal hydroxide is employed, preferably having an alkali metal hydroxide content of from 30 to 70 percent, more preferably from 35 to 60 percent, most preferably from 48 to 52 percent, based on the total weight of the aqueous solution of the alkali metal hydroxide.

In one embodiment, an organic solvent such as dimethyl ether is added to the reactor as a diluent and a coolant. Likewise, the headspace of the reactor is optionally purged with an inert gas (such as nitrogen) to control oxygen-catalyzed depolymerization of the cellulose ether product.

In the first stage of the process the cellulose pulp is treated with a first amount of alkalizing agent, typically from 1.2 to 3.5 molar equivalents of alkalizing agent per mole of anhydroglucose units in the cellulose. The treatment can be conducted by any means known in the art such as by steeping in a bath or stirred tank or spraying. Uniform swelling and distribution of the alkalizing agent in the pulp may be achieved by mixing and agitation. In the first stage the rate of addition of the aqueous solution of the alkalizing agent to the cellulose pulp is not critical. It may be added in several portions, e.g. 2 to 4 portions, or continuously. During first stage alkalization, which usually lasts from 15 to 60 minutes, the temperature is typically maintained at 45° C. or below.

Moreover, a methylating agent such as methyl chloride or dimethyl sulfate is added to the cellulose pulp within the first stage of the process, before, after or concurrently with the first amount of alkalizing agent, preferably after the addition of the alkalizing agent. The methylating agent can be added to the cellulose or, as the reaction of cellulose pulp to the hydroxyalkyl methyl cellulose proceeds, to partially reacted cellulose pulp, in a single stage, but it is preferably added in two or more stages, more preferably two or three stages, most preferably two stages.

If the methylating agent is added in a single stage, it is generally added in an amount of from 3.5 to 6.0 mole of methylating agent per mole of anhydroglucose units, but in any event it is added in at least an equimolar amount, compared to the alkalizing agent added in the first stage, before heating the reaction mixture. If the methylating agent is added in a single stage, it is preferably added at a rate of from 0.25 to 1.0 molar equivalents of methylating agent per mole of anhydroglucose units per minute. The methylating agent used in the first stage may be pre-mixed with any conventional suspending agent. In this case, a mixture comprising from 20 to 50%, more preferably from 30 to 50%, of the suspending agent, based on the total weight of the suspending agent and the at least one methylating agent is preferably employed.

Once the cellulose has been treated with the first amount of alkalizing agent and the additions of the methylating agent and possible further components of the first stage, preferably conducted also at a temperature of 45° C. or below, have been accomplished, the reaction mixture is heated, typically within 30 to 80 minutes, to a reaction temperature of at least 70° C., preferably in the range of 70-90° C., more preferably in the range of 70-80° C. Usually the reaction is then allowed to proceed at this reaction temperature for 10 to 30 minutes.

Subsequently the process comprises at least one additional stage comprising addition of an additional amount of alkalizing agent and, optionally for each individual additional stage, addition of an additional amount of the methylating agent to the reaction mixture. The total amount of additional alkalizing agent added as aqueous solution within the at least one additional stage typically ranges from 1.0 to 2.9 molar equivalents of alkalizing agent per mole of anhydroglucose units. Preferably, the molar equivalent ratio between the amount of alkalizing agent added in the first stage and the amount of alkalizing agent added in total in the at least one additional stage is from 0.6:1 to 3.5:1. It is important to add the alkalizing agent in the at least one additional stage slowly to the reaction mixture, i.e. at a rate of less than 0.055, preferably less than 0.050, more preferably less than 0.045 molar equivalents of alkalizing agent per mole of anhydroglucose units per minute. The alkalizing agent of the second stage is generally added at a temperature of from 50 to 80° C., preferably from 65 to 80° C.

Typically the methylating agent is used in a total amount in the range of 2 to 6 moles per mole of anhydroglucose units. If the methylating agent is added not only in the first stage, but also in at least one additional subsequent stage, preferably in one additional stage, it is typically added in an amount of 2.0 to 4.0 mole of methylating agent per mole of anhydroglucose units in the first stage and in a total amount of 1.5 to 3.4 mole of methylating agent per mole of anhydroglucose units in the at least one additional stages. In any event the methylating agent is added in at least an equimolar amount, compared to the alkalizing agent present in the reaction mixture. Accordingly, the methylating agent of the second stage, if any, is added to the reaction mixture before or during the second and optionally third stage of adding the alkalizing agent in such a manner that the cellulose or, as the reaction of cellulose pulp to the hydroxyalkyl methyl cellulose proceeds, the partially reacted cellulose pulp, is continuously contacted with an at least equimolar equivalent amount of the methylating agent compared to the alkalizing agent.

If the methylating agent is added in two stages, the methylating agent of the first stage is preferably added at a rate of from 0.25 to 0.5 molar equivalents of methylating agent per mole of anhydroglucose units per minute. The methylating agent of the single stage or of the first stage may be pre-mixed with a suspending agent. In this case the mixture of suspending agent and methylating agent preferably comprises from 20 to 50 weight percent, more preferably from 30 to 50 weight percent, of the suspending agent, based on the total weight of methylating agent and suspending agent.

If the methylating agent is added in two stages, the second stage of methylating agent is generally added to the reaction mixture after having heated the reaction mixture to a temperature of about 70-90° C. for 10 to 30 minutes. The methylating agent of the second stage is preferably added at a rate of from 0.25 to 0.5 molar equivalents of methylating agent per mole of anhydroglucose units per minute. If the methylating agent is added in two stages, the molar ratio between the methylating agent of the first stage and the methylating agent of the second stage is generally from 0.68:1 to 1.33:1. The methylating agent in each of the at least one additional stage, if used therein, should be added to the reaction mixture prior to or during the addition of the additional amount of alkalizing agent of that stage in such a manner that the cellulose is continuously contacted with an at least equimolar equivalent amount of the at least one methylating agent compared to the alkalizing agent.

As an alternative to the procedure described above wherein the methylating agent and alkalizing agent each are added in two stages, the methylating agent of the second stage may be added to the reaction mixture after a portion of the alkalizing agent of the second stage has been added, followed by subsequent addition of alkalizing agent; i.e., the methylating agent is added in a second stage, which is followed by the addition of a third stage alkalizing agent. In this embodiment of the process, the total amount of alkalizing agent per mole of anhydroglucose added in the second and third stage is generally 1.0 to 2.9 moles per mole of anhydroglucose units, of which preferably 40 to 60 percent are added in the second stage and 60 to 40 percent are added in the third stage. Preferably the alkalizing agent used in the third stage is added slowly, i.e., at a rate of less than 0.055, typically at a rate of less than 0.045 molar equivalents of alkalizing agent per mole of anhydroglucose units per minute. The methylating agent and alkalizing agent of the third stage are generally added at a temperature of from 50 to 80° C., preferably from 65 to 80° C. One or more, preferably one or two, hydroxyalkylating agents, such as ethylene oxide and/or propylene oxide are also added to the cellulose pulp, or, as the reaction of cellulose pulp to the hydroxyalkyl methyl cellulose proceeds, to partially reacted cellulose pulp, either before, after, or concurrently with the alkalizing agent added in the first stage. A single hydroxyalkylating agent or more than one, preferably only one, hydroxyalkylating agent may be utilized. The hydroxyalkylating agent is generally added in an amount of 0.2 to 2.0 mole of hydroxyalkylating agent per mole of anhydroglucose units. The hydroxyalkylating agent is advantageously added before heating the reaction mixture to the reaction temperature, i.e. at a temperature of from 20 to 70° C., preferably from 40 to 60° C.

An additional alkylating agent, different from a methylating agent, may also be added to the cellulose pulp, either before, after, or concurrently with the alkalizing agent added in the first stage. Non-limiting examples include ethyl chloride, ethyl bromide or ethyl iodide, diethyl sulphate and/or propyl chloride. The additional alkylating agent is generally added in an amount of 0.5 to 6 mole of alkylating agent per mole of anhydroglucose units. The alkylating agent is advantageously added before heating the reaction mixture to the reaction temperature, i.e. at a temperature of from 20 to 70° C., preferably from 40 to 60° C.

After accomplishment of the above described multistage etherification the obtained cellulose ether is typically further purified, dried and/or milled. Usually the cellulose ether is washed to remove salt and other reaction by-products. Any solvent in which the salt formed as a by-product of the etherification reaction is soluble may be employed, but water is usually utilized.

The cellulose ether is optionally subjected to a partial depolymerization process. Partial depolymerization processes are well known in the art and described, for example, in European Patent Applications EP 1,141,029; EP 210,917; EP 1,423,433; and U.S. Pat. No. 4,316,982. Alternatively, partial depolymerization can be achieved during the production of the cellulose ethers, for example by the presence of oxygen or an oxidizing agent. In such partial depolymerization process a cellulose ether can be obtained which has a viscosity of from 2.4 to 200 mPa·s, preferably from 2.4 to 100 mPa·s, more preferably from 2.5 to 50 mPa·s, and most preferably from 3 to 30 mPa·s, determined in a 2% by weight solution in water at 20° C. according to ASTM D2363-79 (Reapproved 2006).

The above-described cellulose ether has free hydroxyl groups which can be esterified with (i) aliphatic monovalent acyl groups or (ii) groups of the formula —C(O)—R—COOA wherein R is a divalent aliphatic or aromatic hydrocarbon group and A is hydrogen or a cation or (iii) a combination of aliphatic monovalent acyl groups and groups of the formula —C(O)—R—COOA. The cation preferably is an ammonium salt or an alkali metal salt, such as a sodium or potassium salt, more preferably a sodium salt. Most preferably, A is hydrogen.

The aliphatic monovalent acyl groups are preferably selected from the group consisting of acetyl, propionyl, and butyryl, such as n-butyryl or i-butyryl. Preferred groups of the formula —C(O)—R—COOA are groups of the formula —C(O)—CH$_2$—CH$_2$—COOA, such as —C(O)—CH$_2$—CH$_2$—COOH or —C(O)—CH$_2$—CH$_2$—COO$^-$Na$^+$, C(O)—CH=CH—COOA, such as —C(O)—CH=CH—COOH or —C(O)—CH=CH—COO$^-$Na$^+$, or —C(O)—C$_6$H$_4$—COOA, such as —C(O)—C$_6$H$_4$—COOH or —C(O)—C$_6$H$_4$—COO$^-$Na$^+$.

In the groups of formula —C(O)—C$_6$H$_4$—COOA, such as —C(O)—C$_6$H$_4$—COOH the carbonyl group and the carboxylic group are preferably arranged in ortho-positions. Preferred esterified cellulose ethers are i) HPMCXY and HPMCX, wherein HPMC is hydroxypropyl methyl cellulose, X is A (acetate), or X is B (butyrate) or X is Pr (propionate) and Y is S (succinate), Y is P (phthalate) or Y is M (maleate), such as hydroxypropyl methyl cellulose acetate phthalate (HPMCAP), hydroxypropyl methyl cellulose acetate maleate (HPMCAM), hydroxypropyl methylcellulose acetate succinate (HPMCAS), or hydroxypropyl methyl cellulose acetate (HPMCA); or ii) hydroxypropyl methyl cellulose phthalate (HPMCP); hydroxypropyl cellulose acetate succinate (HPCAS), hydroxybutyl methyl cellulose propionate succinate (HBMCPrS), hydroxyethyl hydroxypropyl cellulose propionate succinate (HEHPCPrS); and methyl cellulose acetate succinate (MCAS).

Hydroxypropyl methylcellulose acetate succinate (HPMCAS) is the most preferred esterified cellulose ether.

The esterified cellulose ether of the present invention generally has a viscosity of from 2.4 to 200 mPa·s, preferably from 2.4 to 100 mPa·s, more preferably from 2.5 to 50 mPa·s, and most preferably from 3 to 30 mPa·s, measured as a 2.0 weight percent solution of the esterified cellulose ether in 0.43 wt % aqueous NaOH at 20° C. according to "Hypromellose Acetate Succinate, United States Pharmacopia and National Formulary, NF 29, pp. 1548-1550".

The esterified cellulose ethers of the present invention have a DS(methyl) and an MS(hydroxyalkyl) as indicated further above.

The esterified cellulose ethers of the present invention generally have a degree of substitution of monovalent acyl groups, such as acetyl, propionyl, or butyryl groups, of 0 to 2.0, preferably 0.05 to 1.75, more preferably of 0.10 to 1.50, most preferably of 0.15 to 1.25, and particularly of 0.20 to 1.00 or even 0.20 to 0.65.

The esterified cellulose ethers of the present invention generally have a degree of substitution of groups of formula —C(O)—R—COOH, such as succinoyl, of 0 to 2.0, preferably 0 to 1.6, more preferably of 0.05 to 1.30, most preferably of 0.05 to 1.00, and particularly of 0.10 to 0.70 or even 0.10 to 0.60.

The sum of i) the degree of substitution of monovalent acyl groups and ii) the degree of substitution of groups of formula —C(O)—R—COOH is greater than 0. It is generally from 0.05 to 2, preferably from 0.1 to 1.9, more preferably from 0.2 to 1.7, most preferably from 0.3 to 1.55 and particularly from 0.4 to 1.4 or 0.4 to 1.15 or even 0.4 to 1.00.

The ratio of degree of substitution of monovalent acyl groups/degree of substitution of groups of formula —C(O)—R—COOH, such as the ratio of degree of substitution of acetyl groups/degree of substitution of succinoyl groups (DOS$_{Ac}$/DOS$_S$) is generally up to 6.0/1.0 preferably up to 3.0/1.0, more preferably up to 2.7/1.0, and most preferably up to 2.2/1.0. This ratio is typically 0.6/1.0 or more.

The content of the acetate and succinate ester groups is determined according to "Hypromellose Acetate Succinate, United States Pharmacopia and National Formulary, NF 29, pp. 1548-1550". Reported values are corrected for volatiles (determined as described in section "loss on drying" in the above HPMCAS monograph). The method may be used in analogue manner to determine the content of propionyl, butyryl, phthalyl and other ester groups.

The content of ether groups in the esterified cellulose ether is determined in the same manner as described for "Hypromellose", United States Pharmacopeia and National Formulary, USP 35, pp 3467-3469.

The contents of ether and ester groups obtained by the above analyses are converted to DS and MS values of individual substituents according to the formulas below. The formulas may be used in analogue manner to determine the DS and MS of substituents of other cellulose ether esters.

$$\% \text{ cellulose backbone} = 100 - \left(\% \text{ MeO} * \frac{M(OCH_3) - M(OH)}{M(OCH_3)}\right) - \left(\% \text{ HPO} * \frac{M(OCH_2CH(OH)CH_3) - M(OH)}{M(OCH_2CH(OH)CH_3)}\right) - \left(\% \text{ Acetyl} * \frac{M(COCH_3) - M(H)}{M(COCH_3)}\right) - \left(\% \text{ Succinoyl} * \frac{M(COC_2H_4COOH) - M(H)}{M(COC_2H_4COOH)}\right)$$

$$DS(Me) = \frac{\frac{\% \text{ MeO}}{M(OCH_3)}}{\frac{\% \text{ cellulose backbone}}{M(AGU)}}$$

$$MS(HP) = \frac{\frac{\% \text{ HPO}}{M(HPO)}}{\frac{\% \text{ cellulose backbone}}{M(AGU)}}$$

$$DS(Acetyl) = \frac{\frac{\% \text{ Acetyl}}{M(Acetyl)}}{\frac{\% \text{ cellulose backbone}}{M(AGU)}}$$

$$DS(Succinoyl) = \frac{\frac{\% \text{ Succinoyl}}{M(Succinoyl)}}{\frac{\% \text{ cellulose backbone}}{M(AGU)}}$$

$M(MeO) = M(OCH_3) = 31.03 \, Da$ $M(HPO) = M(OCH_2CH(OH)CH_3) = 75.09 \, Da$ $M(Acetyl) = M(COCH_3) = 43.04 \, Da$ $M(Succinoyl) = M(COC_2H_4COOH) = 101.08 \, Da$ $M(AGU) = 162.14 \, Da \quad M(OH) = 17.008 \, Da \quad M(H) = 1.008 \, Da$ By convention, the weight percent is an average weight percentage based on the total weight of the cellulose repeat unit, including all substituents. The content of the methoxyl group is reported based on the mass of the methoxyl group (i.e., —OCH$_3$). The content of the hydroxyalkoxyl group is reported based on the mass of the hydroxyalkoxyl group (i.e., O-alkylene-OH); such as hydroxypropoxyl (i.e., —O—CH$_2$CH(CH$_3$)—OH). The content of the aliphatic monovalent acyl groups is reported based on the mass of —C(O)—R$_1$ wherein R$_1$ is a monovalent aliphatic group, such as acetyl (—C(O)—CH$_3$). The content of the group of formula —C(O)—R—COOH is based on the mass of this group, such as the mass of succinoyl groups (i.e., —C(O)—CH$_2$—CH$_2$—COOH).

It has surprisingly been found that the esterified cellulose ethers of the present invention described above wherein [s23/s26−0.2*MS(hydroxyalkyl)] is not more than 0.36 or 0.33 or 0.31 or 0.30 or 0.27 or 0.25 or 0.23 or 0.21 or even not more than 0.19 (low s23/s26−0.2*MS(hydroxyalkyl) being highly preferred) have an increased tendency to aggregation in aqueous solutions and form larger colloids in aqueous solutions than known comparable esterified cellulose ethers wherein [s23/s26−0.2*MS(hydroxyalkyl)] is higher than the above listed values, specifically more than 0.36. Without wanting to be bound to the theory, applicants believe that the ability of the esterified cellulose ethers to aggregate and to form colloids in aqueous solutions influences and, depending on the drug, improves the solubility of the drug in aqueous solutions and increases its bioavailability, i.e., its in vivo absorption by an individual upon ingestion. The impact of the parameter [s23/s26−0.2*MS(hydroxyalkyl)] is illustrated in FIG. 1 which illustrates the colloid diameter of esterified cellulose ethers of the present invention and of comparative and known comparable esterified cellulose ethers.

The above described esterified cellulose ether is prepared in a process which comprises the step of reacting an above-described cellulose ether with (i) an aliphatic monocarboxylic acid anhydride or (ii) a dicarboxylic acid anhydride or (iii) a combination of an aliphatic monocarboxylic acid anhydride and a dicarboxylic acid anhydride. Preferred aliphatic monocarboxylic acid anhydrides are selected from the group consisting of acetic anhydride, butyric anhydride and propionic anhydride. Preferred dicarboxylic acid anhydrides are selected from the group consisting of succinic anhydride, maleic anhydride and phthalic anhydride. A preferred aliphatic monocarboxylic acid anhydride can be used alone; or a preferred dicarboxylic acid anhydride can be used alone; or a preferred aliphatic monocarboxylic acid anhydride can be used in combination with a preferred dicarboxylic acid anhydride.

The esterification of the cellulose ether can be conducted in a known manner, for example as described in U.S. Pat. Nos. 3,435,027 and 4,226,981, in the International Patent Application WO 2005/115330, or in European Patent Application EP 0 219 426.

According to a first embodiment of the process for preparing an esterified cellulose ether, the esterification of the cellulose ether is conducted in (c) an aliphatic carboxylic acid as a reaction medium, such as acetic acid, propionic acid, or butyric acid. The reaction medium can comprise minor amounts of other solvents or diluents which are liquid at room temperature and do not react with the cellulose ether, such as halogenated $C_1$-$C_3$ derivatives, such as dichloro methane, or dichloro methyl ether, but the amount of the aliphatic carboxylic acid should generally be more than 50 percent, preferably at least 75 percent, and more preferably at least 90 percent, based on the total weight of the reaction medium. Most preferably the reaction medium consists of an aliphatic carboxylic acid. The esterification reaction is generally conducted in the presence of 100 to 2,000 parts by weight of an aliphatic carboxylic acid as the reaction medium per 100 parts by weight of the cellulose ether. The esterification reaction is generally conducted in the presence of (d) an esterification catalyst, preferably in the presence of an alkali metal carboxylate, such as sodium acetate or potassium acetate. The amount of the alkali metal carboxylate is preferably 20 to 200 parts by weight of the alkali metal carboxylate per 100 parts by weight of the cellulose ether. If an aliphatic monocarboxylic acid anhydride and a dicarboxylic acid anhydride are used for esterifying the cellulose ether, the two anhydrides may be introduced into the reaction vessel at the same time or separately one after the other. The amount of each anhydride to be introduced into the reaction vessel is determined depending on the desired degree of esterification to be obtained in the final product, usually being 1 to 10 times the stoichiometric amounts of the desired molar degree of substitution of the anhydroglucose units by esterification. The mixture is generally heated at 60° C. to 110° C., preferably at 70 to 100° C., for a period of time sufficient to complete the reaction, that is, typically from 2 to 25 hours, more typically from 2 to 8 hours.

According to a second embodiment of the process the esterification of the cellulose ether is conducted in an organic solvent, such as acetone or dimethylformamide, in the presence of a basic catalyst, such as pyridine or alpha-picoline. The amount of the organic solvent preferably is 50 to 1,000 parts by weight per 100 parts by weight of the cellulose ether. The amount of the basic catalyst generally is at least equivalent to the acid anhydride(s) to be reacted. The amount of aliphatic monocarboxylic acid anhydride and/or dicarboxylic acid anhydride used for esterifying the cellulose ether is determined depending on the desired degree of esterification to be obtained in the final product, usually being 1 to 10 times the stoichiometric amounts of the desired molar degree of substitution of the anhydroglucose units by esterification. The mixture is generally heated at 40° C. to 120° C., for a period of time sufficient to complete the reaction, that is, typically from 2 to 120 hours.

The cellulose ether as the starting material is not always soluble in the reaction medium, but can only be dispersed in or swollen by the reaction medium. The esterification reaction can take place even with such a dispersed or swollen cellulose ether and, as the esterification reaction proceeds, the cellulose ether under reaction generally dissolves in the reaction medium, to finally give a homogeneous solution. After completion of the esterification reaction, the esterified cellulose ether can be precipitated by contacting the reaction product mixture with a large volume of water, as described in U.S. Pat. No. 4,226,981, in the International Patent Application WO 2005/115330, or in European Patent Application EP 0 219 426. The precipitated esterified cellulose ether can then be subjected to thorough washing with water to remove impurities and dried to produce an esterified in powdery or granular form.

Another aspect of the present invention is a liquid composition which comprises an organic diluent and at least one esterified cellulose ether as described above and optionally an active ingredient and/or adjuvants. The term "liquid" as used herein means liquid at 25° C. and atmospheric pressure. The term "organic diluent" as used herein means an organic solvent or a mixture of two or more organic solvents. Preferred organic diluents are polar organic solvents having one or more heteroatoms, such as oxygen, nitrogen or halogen like chlorine. More preferred organic diluents are alcohols, most preferably multifunctional alcohols, such as glycerol, or monofunctional alcohols, such as methanol, ethanol, isopropanol or n-propanol; ethers, such as tetrahydrofuran, ketones, such as acetone, methyl ethyl ketone, or methyl isobutyl ketone; acetates, such as ethyl acetate; halogenated hydrocarbons, such as methylene chloride; nitriles, such as acetonitrile. More preferably the organic diluents have 1 to 6, most preferably 1 to 4 carbon atoms. The liquid composition of the present invention may additionally comprise water; however, the liquid composition should comprise more than 50, more preferably at least 65, and most preferably at least 75 weight percent of an organic diluent and less than 50, more preferably up to 35, and most preferably up to 25 weight percent of water, based on the total weight of the organic diluent and water. Specific examples of preferred organic diluents, optionally mixed with minor amounts of water are: methanol, tetrahydrofuran, methylene chloride, a blend of 80 to 95 weight percent of methanol and 20 to 5 weight percent of water, a blend of 80 to 95 weight percent of tetrahydrofuran and 20 to 5 weight percent of water, a blend of 55 to 85 weight percent of acetone and 45 to 15 weight percent of water, a blend of 15 to 85 weight percent of acetone and 85 to 15 weight percent of methanol, a blend of 15 to 85 weight percent of methyl ethyl ketone and 85 to 15 weight percent of methanol, a blend of 30 to 50 weight percent of acetonitrile and 70 to 50 weight percent of a $C_{1-4}$-monoalcohol, such as methanol, ethanol, isopropylalcohol, or n-propanol; a blend of 30 to 50 weight percent of methanol and 70 to 50 weight percent of tetrahydrofuran or ethyl acetate, or a blend of 70 to 90 weight percent of ethanol and 10 to 30 weight percent of tetrahydrofuran or ethyl acetate.

In another embodiment the composition of the present invention comprises as liquid diluent water alone or mixed with a minor amount of an organic liquid diluent as described above. In this embodiment the composition of the present invention preferably comprises at least 50, more preferably at least 65, and most preferably at least 75 weight percent of water and preferably up to 50, more preferably up to 35, and most preferably up to 25 weight percent of an organic liquid diluent, based on the total weight of the organic liquid diluent and water. This embodiment of the invention is of particularly useful for providing coatings or capsules from aqueous compositions comprising the esterified cellulose ether of the present invention. When preparing an aqueous solution, it is preferred that at least a portion of the groups of formula —C(O)—R—COOA are in their salt form.

Another aspect of the present invention is a solid dispersion of at least one active ingredient in at least one esterified cellulose ether of the present invention as described above. By "solid dispersion" as used herein is meant that at least a portion of the drug is dispersed in the esterified cellulose ether. Preferably the solid dispersion is a solid amorphous dispersion wherein at least the major portion, more preferably at least 90 wt %, most preferably 100% of the active ingredient is in amorphous form and dispersed in the esterified cellulose ether. The term "amorphous" as used herein means that the active ingredient does not have a long-range three-dimensional translational order.

The esterified cellulose ethers comprised in the liquid compositions of the present invention and in the solid dispersions of the present invention are able to maintain the concentration of poorly water-soluble active ingredients, such as poorly water-soluble drugs in aqueous solutions at supersaturation levels. A considerably higher concentration of a poorly water-soluble active ingredient in an aqueous solution can be maintained than in the absence of an esterified cellulose ether described above. The degree of supersaturation of a poorly water-soluble active ingredient in an aqueous solution depends on various factors, such as the physical stability and the dissolution rate of a given active ingredient. Dwayne T. Friesen et al. in MOLECULAR PHARMACEUTICS VOL. 5, NO. 6, 1003-1019, 2008 have classified compounds with a structurally diverse range of physicochemical properties on a physical property map Tm/Tg ratio versus log P.

The log P value is a standard measure of the lipophilicity of a compound. Log P, defined as the base 10 logarithm of the ratio of (1) the drug concentration in an octanol phase to (2) the drug concentration in a water phase when the two phases are in equilibrium with each other, is a widely accepted measure of hydrophobicity. Log P may be measured experimentally or calculated using methods known in the art. When using a calculated value for Log P, the highest value calculated using any generally accepted method for calculating Log P is used. Calculated Log P values are often referred to by the calculation method, such as Clog P, Alog P, and Mlog P. The Log P may also be estimated using fragmentation methods, such as Crippen's fragmentation method (27 J. Chem. Inf. Comput. Sci. 2 1 (1987)); Viswanadhan's fragmentation method (29 J. Chem. Inf. Comput. Sci. 163 (1989)); or Broto's fragmentation method (19 Eur. J. Med. Chem.-Chim Theor. 7 1 (1984)).

$$\log P_{oct/wat} = \log\left(\frac{[\text{solute}]_{octanol}}{[\text{solute}]_{water}^{un-ionized}}\right)$$

Compounds with high log P values are very hydrophobic and tend to have extremely low water solubilities (often less than 1 µg/mL when their melting points are above about 100° C.) and low propensities for wetting when placed into water.

Tm is the melting temperature and Tg is the glass transition temperature of the compound at atmospheric pressure. Dwayne T. Friesen et al. have divided the compounds into four groups based on their position on this physical property map Tm/Tg ratio versus log P (FIG. 14 on page 1018 in MOLECULAR PHARMACEUTICS VOL. 5, NO. 6, 2008). The first group, Group 1, consists of compounds with relatively low Tm/Tg ratios (<1.25 K/K) and low to moderate log P values (less than about 6); Compounds in Group 2 have somewhat higher Tm/Tg ratios (1.25-1.4) and low to moderate log P values (less than about 6). Compounds in Group 3 have even higher Tm/Tg values (greater than 1.4) and low to moderate log P values (less than about 6). Finally, Group 4 compounds, have high log P values (at least about 6).

It has surprisingly been found that some of the esterified cellulose ethers of the present invention described above wherein [s23/s26−0.2*MS(hydroxyalkyl)] is not more than 0.36 or 0.33 or 0.31 or 0.30 or 0.27 or 0.25 or 0.23 or 0.21 or even not more than 0.19 (low s23/s26−0.2*MS(hydroxyalkyl) being highly preferred) have a higher ability to keep some active ingredients at a supersaturation level in an aqueous solution than known comparable esterified cellulose ethers wherein [s23/s26−0.2*MS(hydroxyalkyl)] is higher than the above listed values, specifically more than 0.36.

For example the drug Griseofulvin, which has a very low water solubility of 8.54 mg/l and belongs to group 2 on the map Tm/Tg ratio versus log P (FIG. 14 on page 1018 in MOLECULAR PHARMACEUTICS VOL. 5, NO. 6, 2008) has a higher concentration in the presence of some of the esterified cellulose ethers of the present invention than in the presence of known comparable esterified cellulose ethers Accordingly, a preferred aspect of the present invention is a liquid composition or a solid dispersion of the present invention which comprises at least one esterified cellulose ether of the present invention as described above and additionally at least one active ingredient that has a Tm/Tg ratio of more than 1.0 up to 1.8, preferably more than 1.1 up to 1.6, more preferably 1.15 up to 1.5, most preferably 1.25 up to 1.40, wherein the melting temperature Tm and the glass transition temperature Tg each are in Kelvin. The active ingredient preferably has a log P of more than 1 up to 11, preferably more than 2 up to 10, most preferably 2.5 up to 8.

The active ingredient does not need to be a low-solubility active ingredient in order to benefit from this invention, although low-solubility active ingredients represent a preferred class for use with the invention. An active ingredient that exhibits appreciable aqueous solubility in the desired environment of use may have an aqueous solubility up to 1 to 2 mg/mL, or even as high as 20 to 40 mg/mL. Useful low-solubility drugs are listed in the International Patent Application WO 2005/115330, pages 17-22.

The liquid composition of the present invention preferably comprises from 0.2 to 40 weight percent, more preferably from 0.5 to 30 weight percent, most preferably from 3 to 25 weight percent, and particularly from 5 to 20 percent of at least one esterified cellulose ether as described above, from 40 to 99.8 weight percent, more preferably from 54.9 to 99.4 weight percent, most preferably from 65 to 96.5 weight percent and particularly from 70 to 94 percent of an organic or aqueous diluent, and from 0 to 40 percent, preferably from 0.1 to 40 percent, most preferably from 0.5 to 25 percent, and particularly from 1 to 15 percent of an active ingredient, based on the total weight of the liquid composition.

In one aspect of the invention the liquid composition of the present invention comprising at least one esterified cellulose ether as described above, one or more active ingredients and optionally one or more adjuvants can be used in liquid form, for example in the form of a suspension, a sprayable composition, or a syrup. The liquid composition is useful, e.g., for oral, ocular, topical, rectal or nasal applications. The liquid diluent should generally be pharmaceutically acceptable, such as ethanol or glycerol, optionally mixed with minor amounts of water as described above.

In another aspect of the invention the esterified cellulose ether of the present invention is used for producing a solid dispersion of at least one active ingredient, such as a drug described further above, in at least one esterified cellulose ether as described above and optionally one or more adjuvants. The solid dispersion can be produced by removing the liquid diluent from the liquid composition described above. One method of removing the liquid diluent from the liquid composition is by casting the liquid composition into a film or a capsule or by applying the liquid composition onto a solid carrier that in turn may comprise an active ingredient. A preferred method of producing the solid dispersion is by spray-drying. The term "spray-drying" refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50 Chem. Eng. Prog. Monogr. Series 2 (1954), and Masters, Spray Drying Handbook (Fourth Edition 1985). A useful spray-drying process is described in the International Patent Application WO 2005/115330, page 34, line 7—page 35, line 25. The solid dispersion of the present invention preferably comprises from 20 to 99.9 percent, more preferably from 30 to 98 percent, and most preferably from 50 to 95 percent of an esterified cellulose ether a) of the present invention as described above, and preferably from 0.1 to 80 percent, more preferably from 2 to 70 percent, and most preferably from 5 to 50 percent of an active ingredient b), based on the total weight of the esterified cellulose ether a) and the active ingredient b). The combined amount of the esterified cellulose ether a) and the active ingredient b) is preferably at least 70 percent, more preferably at least 80 percent, and most preferably at least 90 percent, based on the total weight of the solid dispersion. Once the solid dispersion of at least one active ingredient in at least one esterified cellulose ether has been formed, several processing operations can be used to facilitate incorporation of the dispersion into a dosage form. These processing operations include drying, granulation, and milling. The inclusion of optional adjuvants in the solid dispersion may be useful in order to formulate the composition into dosage forms, such as tablets, pills, granules, pellets, caplets microparticles, fillings of capsules, or into pastes, creams, suspensions or slurries.

In another aspect of the invention the liquid composition of the present invention may be used for coating dosage forms, such as tablets, granules, pellets, caplets, lozenges, suppositories, pessaries or implantable dosage forms, to form a coated composition. If the liquid composition of the present invention comprises an active ingredient, such as a drug, drug layering can be achieved, i.e., the dosage form and the coating may comprise different active ingredients for different end-uses and/or having different release kinetics.

In yet another aspect of the invention the liquid composition of the present invention may be used for the manufacture of capsules in a process which comprises the step of contacting the liquid composition with dipping pins.

The liquid composition and the solid dispersion of the present invention may further comprise optional additives, such as coloring agents, pigments, opacifiers, flavor and taste improvers, antioxidants and any combination thereof. Useful amounts and types of one or more optional adjuvants are generally known in the art and depend on the intended end-use of the liquid composition or the solid dispersion of the present invention.

The following examples are for illustrative purposes only and are not intended to limit the scope of the present invention. All percentages are by weight unless otherwise specified.

EXAMPLES

The viscosity of the hydroxypropyl methylcellulose acetyl succinate (HPMCAS) is measured as a 2.0 weight percent solution of the HPMCAS in 0.43 wt % aqueous NaOH at 20° C. according to "Hypromellose Acetate Succinate, United States Pharmacopia and National Formulary, NF 29, pp. 1548-1550". The viscosity of the hydroxypropyl methylcellulose (HPMC) used as a starting material for producing HPMCAS is measured as a 2% by weight solution in water at 20° C. according to ASTM D2363—79 (Reapproved 2006).

The determination of the % methoxyl and % hydroxypropoxyl in HPMC used as a starting material for producing HPMCAS is carried out according to the United States Pharmacopeia (USP 35). The % methoxyl and % hydroxypropoxyl of HPMCAS are determined in the same manner as described for "Hypromellose", United States Pharmacopeia and National Formulary, USP 35, pp 3467-3469. The values obtained as % methoxyl and % hydroxypropoxyl are subsequently converted into degree of substitution (DS) for methyl substituents and molar substitution (MS) for hydroxypropyl substituents. Residual amounts of salt are taken into account in the conversion.

The determination of the % succinoyl and % acetyl in HPMCAS is carried out according to "Hypromellose Acetate Succinate, United States Pharmacopeia and National Formulary, NF 30, pp 1824-1826". Reported values are corrected for volatiles (determined as described in section "loss on drying" in the above HPMCAS monograph).

Determination of s23/s26 of HPMC

The determination of ether substituents in ellulose ethers is generally known and e.g., described in Carbohydrate Research, 176 (1988) 137-144, Elsevier Science Publishers B. V., Amsterdam, DISTRIBUTION OF SUBSTITUENTS IN O-ETHYL-O-(2-HYDROXYETHYL)CELLULOSE by Bengt Lindberg, Ulf Lindquist, and Olle Stenberg.

Specifically, determination of s23/s26 is conducted as follows: 10-12 mg of the cellulose ether are dissolved in 4.0 mL of dry analytical grade dimethyl sulfoxide (DMSO) (Merck, Darmstadt, Germany, stored over 0.3 nm molecular sieve beads) at about 90° C. under stirring and then cooled down to room temperature again. The solution is left stirring at room temperature over night to ensure complete solubilization. The entire reaction including the solubilization of the cellulose ether is performed using a dry nitrogen atmosphere in a 4 mL screw cap vial. After solubilization the dissolved cellulose ether is transferred to a 22 mL screw cap vial. Powdered sodium hydroxide (freshly pestled, analytical grade, Merck, Darmstadt, Germany) and ethyl iodide (for synthesis, stabilized with silver, Merck-Schuchardt, Hohenbrunn, Germany) in a thirty fold molar excess of the reagents sodium hydroxide and ethyl iodide per hydroxyl group of the anhydroglucose unit are added and the solution is vigorously stirred under nitrogen in the dark for three days at ambient temperature. The perethylation is repeated with addition of the threefold amount of the reagents sodium hydroxide and ethyl iodide compared to the first reagent addition and further stirring at room temperature for additional two days. Optionally the reaction mixture can be diluted with up to 1.5 mL DMSO to ensure good mixing during the course of the reaction. 5 mL of 5% aqueous sodium thiosulfate solution is poured into the reaction mixture and the obtained solution is then extracted three times with 4 mL of dichloromethane. The combined extracts are washed three times with 2 mL of water. The organic phase is dried with anhydrous sodium sulfate (ca. 1 g). After filtration the solvent is removed in a gentle stream of nitrogen and the sample is stored at 4° C. until further sample preparation.

Hydrolysis of about 5 mg of the perethylated samples is performed under nitrogen in a 2 mL screw cap vial with 1 mL of 90% aqueous formic acid under stirring at 100° C. for 1 hour. The acid is removed in a stream of nitrogen at 35-40° C. and the hydrolysis is repeated with 1 mL of 2M aqueous trifluoroacetic acid for 3 hours at 120° C. in an inert nitrogen atmosphere under stirring. After completion the acid is removed to dryness in a stream of nitrogen at ambient temperature using ca. 1 mL of toluene for co-distillation.

The residues of the hydrolysis are reduced with 0.5 mL of 0.5 M sodium borodeuteride in 2N aqueous ammonia solution (freshly prepared) for 3 hours at room temperature under stirring. The excess reagent is destroyed by drop wise addition of ca. 200 µL of concentrated acetic acid. The resulting solution is evaporated to dryness in a stream of nitrogen at ca. 35-40° C. and subsequently dried in vacuum for 15 min at room temperature. The viscous residue is dissolved in 0.5 mL of 15% acetic acid in methanol and evaporated to dryness at room temperature. This is done five times and repeated four times with pure methanol. After the final evaporation the sample is dried in vacuum overnight at room temperature.

The residue of the reduction is acetylated with 600 µL of acetic anhydride and 150 µL of pyridine for 3 hrs at 90° C. After cooling the sample vial is filled with toluene and evaporated to dryness in a stream of nitrogen at room temperature. The residue is dissolved in 4 mL of dichloromethane and poured into 2 mL of water and extracted with 2 mL of dichloromethane. The extraction is repeated three times. The combined extracts are washed three times with 4 mL of water and dried with anhydrous sodium sulfate. The dried dichloromethane extract is subsequently submitted to GC analysis. Depending on the sensitivity of the GC system, a further dilution of the extract can be necessary.

Gas-liquid (GLC) chromatographic analyses are performed with Hewlett Packard 5890A and 5890A Series II type of gas chromatographs equipped with J&W capillary columns DB5, 30 m, 0.25 mm ID, 0.25 µm phase layer thickness operated with 1.5 bar helium carrier gas. The gas chromatograph is programmed with a temperature profile that holds constant at 60° C. for 1 min, heats up at a rate of 20° C./min to 200° C., heats further up with a rate of 4° C./min to 250° C., heats further up with a rate of 20° C./min to 310° C. where it is held constant for another 10 min. The injector temperature is set to 280° C. and the temperature of the flame ionization detector (FID) is set to 300° C. 1 µL of the samples is injected in the splitless mode at 0.5 min valve time. Data are acquired and processed with a LabSystems Atlas work station.

Quantitative monomer composition data are obtained from the peak areas measured by GLC with FID detection. Molar responses of the monomers are calculated in line with the effective carbon number (ECN) concept but modified as described in the table below. The effective carbon number (ECN) concept has been described by Ackman (R. G. Ackman, J. Gas Chromatogr., 2 (1964) 173-179 and R. F. Addison, R. G. Ackman, J. Gas Chromatogr., 6 (1968) 135-138) and applied to the quantitative analysis of partially alkylated alditol acetates by Sweet et. al (D. P. Sweet, R. H. Shapiro, P. Albersheim, Carbohyd. Res., 40 (1975) 217-225).

ECN increments used for ECN calculations:

| Type of carbon atom | ECN increment |
| --- | --- |
| hydrocarbon | 100 |
| primary alcohol | 55 |
| secondary alcohol | 45 |

In order to correct for the different molar responses of the monomers, the peak areas are multiplied by molar response factors MRFmonomer which are defined as the response relative to the 2,3,6-Me monomer. The 2,3,6-Me monomer is chosen as reference since it is present in all samples analyzed in the determination of s23/s26.

MRFmonomer=ECN2,3,6-Me/ECNmonomer

The mole fractions of the monomers are calculated by dividing the corrected peak areas by the total corrected peak area according to the following formulas:

$$s23=[(23\text{-Me}+23\text{-Me-6-HAMe}+23\text{-Me-6-HA}+23\text{-Me-6-HAHAMe}+23\text{-Me-6-HAHA}];\text{ and}$$

$$s26=[(26\text{-Me}+26\text{-Me-3-HAMe}+26\text{-Me-3-HA}+26\text{-Me-3-HAHAMe}+26\text{-Me-3-HAHA}], \text{ wherein}$$

s23 is the sum of the molar fractions of anhydroglucose units which meet the following conditions:
a) the two hydroxy groups in the 2- and 3-positions of the anhydroglucose unit are substituted with methyl groups and the 6-position is not substituted (=23-Me);
b) the two hydroxy groups in the 2- and 3-positions of the anhydroglucose unit are substituted with methyl groups and the 6-position is substituted with methylated hydroxyalkyl (=23-Me-6-HAMe) or with a methylated side chain comprising 2 hydroxyalkyl groups (=23-Me-6-HAHAMe); and
c) the two hydroxy groups in the 2- and 3-positions of the anhydroglucose unit are substituted with methyl groups and the 6-position is substituted with hydroxyalkyl (=23-Me-6-HA) or with a side chain comprising 2 hydroxyalkyl groups (=23-Me-6-HAHA). s26 is the sum of the molar fractions of anhydroglucose units which meet the following conditions:

a) the two hydroxy groups in the 2- and 6-positions of the anhydroglucose unit are substituted with methyl groups and the 3-position is not substituted (=26-Me);

b) the two hydroxy groups in the 2- and 6-positions of the anhydroglucose unit are substituted with methyl groups and the 3-position is substituted with methylated hydroxyalkyl (=26-Me-3-HAMe) or with a methylated side chain comprising 2 hydroxyalkyl groups (=26-Me-3-HAHAMe); and c) the two hydroxy groups in the 2- and 6-positions of the anhydroglucose unit are substituted with methyl groups and the 3-position is substituted with hydroxyalkyl (=26-Me-3-HA) or with a side chain comprising 2 hydroxyalkyl groups (=26-Me-3-HAHA).

The results of the determination of the substituents in the HAMC are listed in Table 1 and 2 below. In the case of HPMC's hydroxyalkyl (HA) is hydroxypropyl (HP) and methylated hydroxyalkyl (HAMe) is methylated hydroxypropyl (HPMe).

Determination of s23/s26 of HPMCAS

In a first step the HPMCAS is subjected to deacylation, specifically quantatively removing the acetyl and succinoyl groups. Deacylation of esterified cellulose ethers is generally known in the art.

In the procedure used herein 10-12 mg of the esterified cellulose ether are dissolved in 4.0 mL of dry analytical grade dimethyl sulfoxide (DMSO) (Merck, Darmstadt, Germany, stored over 0.3 nm molecular sieve beads) at about 90° C. under stirring for about 2 hours and then cooled down to room temperature again. The entire procedure including the solubilization of the esterified cellulose ether is performed using a dry nitrogen atmosphere in a 4 mL screw cap vial. After solubilization the dissolved esterified cellulose ether is transferred to a 22 mL screw cap vial. 200 mg Powdered sodium hydroxide (freshly pestled, analytical grade, Merck, Darmstadt, Germany) is added and the mixture is stirred under nitrogen for 45 min. Then 500 µL of water is added to the mixture and the mixture is stirred for 1 hour at 60° C. Further 2.5 mL of water is added and the mixture is stirred over night at 60° C. After the mixture in the form of a solution has been cooled down to ambient temperature it is transferred to a dialysis tube (Spectra/Por Dialysis Membrane, Molecular Weight Cut Off 3,500, Spectrum Laboratories, Inc., Rancho Dominguez, Calif. 90220, USA) for clean-up. Water was exchanged at regular intervals during dialysis for 2 days. The contents of the dialysis tube were subjected to freeze-drying to obtain a solid HPMC. The HPMC is analyzed as described above.

Example 1

1A) Preparation of hydroxypropyl methylcellulose (HPMC)

Finely ground wood cellulose pulp was loaded into a jacketed, agitated reactor. The reactor was evacuated and purged with nitrogen to remove oxygen and then evacuated again. The reaction was carried out in two stages. In the first stage a 50 weight percent aqueous solution of sodium hydroxide was sprayed onto the cellulose in an amount of 2.0 moles of sodium hydroxide per mole of anhydroglucose units in the cellulose and the temperature was adjusted to 40° C. After stirring the mixture of aqueous sodium hydroxide solution and cellulose for about 20 minutes at 40° C., 1.5 moles of dimethyl ether, 2.5 moles of methyl chloride and 0.44 mole of propylene oxide per mole of anhydroglucose units were added to the reactor. The contents of the reactor were then heated in 60 min to 80° C. After having reached 80° C., the first stage reaction was allowed to proceed for 5 min.

Then the reaction was cooled down to 50° C. within 20 min. The second stage of the reaction was started by addition of methyl chloride in an amount of 2.5 molar equivalents of methyl chloride per mole of anhydroglucose units. The addition time for methyl chloride was 10 min. Then a 50 weight percent aqueous solution of sodium hydroxide at an amount of 2.0 mole of sodium hydroxide per mole of anhydroglucose units was added over a time period of 45 min. The rate of addition was 0.044 mole of sodium hydroxide per mole of anhydroglucose units per minute. After the second stage addition was completed the contents of the reactor were heated up to 80° C. within 30 min and are then kept at a temperature of 80° C. for 120 min.

After the reaction the reactor was vented and cooled down to about 50° C. The contents of the reactor were removed and transferred to a tank containing hot water. The crude HPMC was then neutralized with formic acid and washed chloride free with hot water (assessed by $AgNO_3$ flocculation test), cooled to room temperature and dried at 55° C. in an air-swept drier. The material was then ground using an Alpine UPZ mill using a 0.5 mm screen.

The obtained powder was partially depolymerized in a known manner by heating the powderous samples with up to 3.0 g gaseous hydrogen chloride per kg of powder at a temperature of at most 85° C. until the desired viscosity was achieved. The partially depolymerized hydroxypropyl methylcellulose was neutralized with sodium bicarbonate. The produced low viscosity HPMC had a DS(methyl) of 2.00, a MS(hydroxypropyl) of 0.18, an s23/s26 of 0.32, a viscosity of 4.7 mPa·s, measured as a 2% by weight solution in water at 20° C., and a [s23/s26−0.2*MS(hydroxypropyl)] of 0.28.

1B) Preparation of Hydroxypropyl Methyl Cellulose Acetate Succinate (HPMCAS)

680.0 g of glacial acetic acid, 243.8 g of acetic anhydride, 190.7 g (dry content 98.3%) of the low viscosity HPMC produced under 1A) above, 52.5 g of succinic anhydride and 187.5 g of sodium acetate (water free) were introduced into a jacketed reactor equipped with a thermostat and an MIG™ stirrer (two blade axial flow impeller, company EKATO, Schopfheim, Germany). The mixture was heated to 85° C. during a time period of 40 minutes and kept at this temperature for 3 hours while stirring the reaction mixture to effect esterification. Subsequently distilled water of a temperature of 22° C. was added to precipitated HPMCAS. The supernatant liquor was removed. The solid material was re-suspended in water while stirring using an Ultra-Turrax stirrer. The suspension was subjected to filtration. The fine particles were washed with water. The HPMCAS was dried at 50-55° C. over night and subsequently ground.

Example 2

HPMC was produced as described in Example 1A, except that after finishing the first stage reaction with proceeding at 80° C. for 5 min, the reaction was cooled down to 50° C. within 20 min. The second stage of the reaction was started by addition of methyl chloride in an amount of 2.5 molar equivalents of methyl chloride per mole of anhydroglucose units. The addition time for methyl chloride was 10 min. Then a 50 weight percent aqueous solution of sodium hydroxide at an amount of 2.0 mole of sodium hydroxide per mole of anhydroglucose units was added over a time period of 90 min. The rate of addition was 0.022 mole of sodium hydroxide per mole of anhydroglucose units per minute.

The produced HPMC was partially depolymerized as described in Example 1A. The low viscosity HPMC had a DS(methyl) of 1.97, an MS(hydroxypropyl) of 0.17, an s23/s26 of 0.29, a viscosity of 4.9 mPa·s, measured as a 2% by weight solution in water at 20° C., and a [s23/s26−0.2*MS(hydroxypropyl)] of 0.26.

HPMCAS is produced as in Example 1B using 700.0 g of glacial acetic acid, 243.8 g of acetic anhydride, 190.9 g (dry content 98.2%) of the low viscosity HPMC, 52.5 g of succinic anhydride and 187.5 g of sodium acetate (water free).

Example 3

Finely ground wood cellulose pulp was loaded into a jacketed, agitated reactor. The reactor was evacuated and purged with nitrogen to remove oxygen and then evacuated again. The reaction was carried out in two stages. In the first stage a 50 weight percent aqueous solution of sodium hydroxide was sprayed onto the cellulose in an amount of 2.0 mole of sodium hydroxide per mole of anhydroglucose units in the cellulose and the temperature was adjusted to 40° C. After stirring the mixture of aqueous sodium hydroxide solution and cellulose for about 20 minutes at 40° C., 1.5 mole of dimethyl ether, 2.5 mole of methyl chloride and 0.8 mole of propylene oxide per mole of anhydroglucose units were added to the reactor. The contents of the reactor were then heated in 60 min to 80° C. After having reached 80° C., the first stage reaction was allowed to proceed for 30 min.

The second stage of the reaction was started by addition of methyl chloride in an amount of 2.8 molar equivalents of methyl chloride per mole of anhydroglucose units. The addition time for methyl chloride was 10 min. Then a 50 weight percent aqueous solution of sodium hydroxide at an amount of 2.3 mole of sodium hydroxide per mole of anhydroglucose units was added over a time period of 90 min. The rate of addition was 0.026 mole of sodium hydroxide per mole of anhydroglucose units per minute. After the second stage addition was completed the contents of the reactor were then kept at a temperature of 80° C. for 120 min.

After the reaction the reactor was vented and cooled down to about 50° C. The contents of the reactor were removed, further processed and then partially depolymerized as described in Example 1A. The produced low viscosity HPMC had a DS(methyl) of 1.83, an MS(hydroxypropyl) of 0.28, an s23/s26 of 0.22, a viscosity of 4.9 mPa·s, measured as a 2% by weight solution in water at 20° C., and a [s23/s26−0.2*MS(hydroxyalkyl)] of 0.16.

HPMCAS was produced as in Example 1 using 143.3 g of glacial acetic acid, 65.0 g of acetic anhydride, 52.03 g (dry content 96.1%) of the low viscosity HPMC, 14.0 g of succinic anhydride and 50.0 g of sodium acetate (water free). After reaction for 3.5 hours water was added and the mixture was cooled to room temperature. The solid product was re-suspended in water while stirring using an Ultra-Turrax stirrer. The suspension was subjected to filtration and twice re-suspended in water and filtered to wash the product. The HPMCAS was dried at 50-55° C. over night and subsequently ground.

Comparative Example A

A commercially available HPMC having a methoxyl content of 30.1%, a hydroxypropoxyl content of 9.9% and a viscosity of about 4000 mPa·s measured as a 2 wt % solution in water at 20° C., was partially depolymerized as described in Example 1A. The low viscosity HPMC had a viscosity of 4.5 mPa·s, measured as a 2% by weight solution in water at 20° C., and a s23/s26−0.2*MS(hydroxyalkyl) of 0.39.

500.0 g of glacial acetic acid, 243.8 g of acetic anhydride, 192.3 g (dry content 97.53%) of the low viscosity HPMC, 52.5 g of succinic anhydride and 187.5 g of sodium acetate (water free) were introduced into a 3 L jacketed reactor equipped with a thermostat and an MIG™ stirrer (two blade axial flow impeller, company EKATO, Schopfheim, Germany). The mixture was heated to 85° C. during a time period of 40 minutes and kept at this temperature for 3 hours while stirring the reaction mixture to effect esterification. Subsequently distilled water of a temperature of 22° C. was added to precipitated HPMCAS. The supernatant liquor was removed. The solid material was re-suspended in water while stirring using an Ultra-Turrax stirrer. The suspension was subjected to filtration. The fine particles were washed with water. The HPMCAS was dried at 50-55° C. over night and subsequently ground.

Comparative Examples B and C

Comparative Examples B and C were two grades of HPMCAS which are commercially available from Shin-Etsu Chemical as Aqoat L grade and M grade. Comparative Example B was an L grade and had a lower ratio of acetate/succinate substitution than Examples 1-3. Comparative Example C was an M grade and had a slightly higher ratio of acetate/succinate substitution than Examples 1-3.

Colloidal Nature of HPMCAS

The colloidal nature of the HPMCAS of Examples 1-3 and Comparative Examples A-C was evaluated The HPMCAS samples were dissolved at 1 wt % in a pH 6.5 phosphate buffered solution (82 mM sodium chloride, 20 mM sodium phosphate dibasic, 47 mM potassium phosphate monobasic) by agitation for 16 h at room temperature. Samples were filtered through a syringe filter (2.7 µm pore size GFD w/GMF, Whatman) before analysis at 37° C. on a Malvern Zetasizer Nano. The size of the colloids that passed through the filter were measured and are shown in FIG. 1. Mono- and multimodal distributions were observed. In the case of multimodal distributions the main peak was 99.4-99.0% of the total HPMCAS number distribution. Only the mean diameter of the colloidal species of the filtrate of the main peak is listed in Table 2 below. Although the HPMCAS of Example 3 does not appear to have the largest colloids according to FIG. 1, filtration tests showed that HPMCAS of Example 3 formed the largest colloids; it was much more difficult to filter than the other HPMCAS samples and much less liquid could be pushed through the syringe filter before the filter clogged completely. The large colloids held back on the filter are not shown in FIG. 1. When Example 3 was not filtered, colloids were too large for accurate size determination by dynamic light scattering.

Impact of HPMCAS on the Aqueous Solubility of a Poorly Soluble Drug

The ability of the HPMCAS of Examples 1 to 3 and of Comparative Examples A to C to maintain drug concentrations in an aqueous solution at supersaturation levels was tested with the poorly water soluble drugs Griseofulvin and Phenytoin.

Griseofulvin has a water solubility of 8.54 mg/l, a log P of 2.2, a Tm of 220° C., a Tg of 85° C., and, accordingly a Tm/Tg=493° K/358° K=1.39. [Feng, Tao et. al.; J. Pharm. Sci.; Vol. 97, No. 8, 2008, pg 3207-3221 and W. Curatolo, Pharmaceutical Research, Vol. 26, No. 6, June 2009, pg 1422]. Griseofulvin belongs to group 2 on the map Tm/Tg ratio versus log P (FIG. 14 on page 1018 in MOLECULAR PHARMACEUTICS VOL. 5, NO. 6).

Phenytoin has a water solubility of 32 mg/l, a log P of 2.47, a Tm of 295° C., a Tg of 71° C. and, accordingly a Tm/Tg=568° K/344° K=1.65 [Friesen et al., MOLECULAR PHARMACEUTICS VOL. 5, NO. 6, 1003-1019 and W. Curatolo, Pharmaceutical Research, Vol. 26, No. 6, June 2009, pg 1422]. Phenytoin belongs to group 3 on the map Tm/Tg ratio versus log P (FIG. 14 on page 1018 in MOLECULAR PHARMACEUTICS VOL. 5, NO. 6).

Solutions of a HPMCAS listed in Table 1 below (950 µl, 3.16 mg/L) in phosphate buffered saline (82 mM sodium chloride, 20 mM sodium phosphate dibasic, 47 mM potassium phosphate monobasic, 0.5 wt % simulated intestinal fluid powder, pH 6.5) at 37° C. were robotically delivered into designated 1 mL vials arranged in an aluminum 96 (8×12) well block heated to 37° C. using a Tecan 150 liquid handler. Organic drug solutions at 37° C. were dispensed onto the phosphate buffered saline aqueous solution comprising a HPMCAS listed in Table 1 below. The organic drug solution was a) 20 g/L griseofulvin in dimethylformamide, 50 µL, final maximum drug concentration of 1000 mg/L, or b) 20 g/L phenytoin in dimethylformamide, 50 µL, final maximum drug concentration of 1000 mg/L The robot aspirated and dispensed liquid in a set sequence for each vial for about 30 s to mix. After 180 minutes the vials were centrifuged 1 min at about 3200×g (g=gravitational force on earth). An aliquot (30 µl) was transferred to methanol (150 µl) in a 96-well plate, sealed, briefly gently agitated to mix, and then the drug concentration was analyzed by HPLC.

In a Control Run the experiment was repeated with a phosphate buffered saline aqueous solution which did not contain any amount of esterified cellulose ether.

In Table 2 below the concentrations of Griseofulvin and Phenytoin are listed that have not precipitated upon centrifugation after 180 minutes but that remain dissolved in the phosphate buffered saline aqueous solution.

The results in Table 1 below illustrate that the esterified cellulose ethers comprised in the liquid compositions and in the solid dispersions of the present invention are able to maintain the concentration of poorly water-soluble drugs in an aqueous solution at supersaturation levels. A considerably higher drug concentration in an aqueous solution can be maintained than in the Control Run in the absence of an esterified cellulose ether. Moreover, the results in Table 2 below illustrate that the esterified cellulose ethers of the present invention have an increased tendency to aggregation in aqueous solutions and form larger colloids in aqueous solutions than esterified cellulose ethers that are known or outside the scope of the present invention and that have a comparable type and degree of the individual ester substituents. Without wanting to be bound to the theory, applicants believe that the ability of the esterified cellulose ethers to aggregate and to form colloids in aqueous solutions influences and, depending on the drug, improves the solubility of the drug in aqueous solutions and increases its bioavailability, i.e., its in vivo absorption by an individual upon ingestion.

Moreover, the HPMCAS of Example 3 is able to maintain a higher concentration of the drug Griseofulvin in aqueous solution than Comparative Example C although the HPMCAS of Example 3 has a very similar $DOS_{Ac}$, $DOS_s$ and ratio of acetyl/succinoyl substitution as the HPMCAS of Comparative Example C. The medium ratio of acetyl/succinoyl substitution of Example 3 provides solubility in aqueous media at a lower pH than HPMCAS of a high acetyl/succinoyl substitution, such as Aqoat H grade from Shin-Etsu Chemical which has a dissolution pH of 6.8 (MOLECULAR PHARMACEUTICS VOL. 5, NO. 6, page 1005, 2008 referring to the Shin-Etsu Product literature). For example, HPMCAS of Example 3 is soluble in the upper part of the intestine of the human body.

TABLE 1

| HPMCAS of (Comparative) Example | Methoxyl (%) | Hydroxypropoxyl (%) | Acetyl (%) | Succinoyl (%) | $DS_M$ | $MS_{HP}$ | $DOS_{Ac}$ | $DOS_s$ | $DOS_{Ac}/DOS_s$ [1] | s23/s26 - 0.2*MS (hydroxypropyl) [2] | s23/s26 - 0.2*MS (hydroxypropyl) [3] |
|---|---|---|---|---|---|---|---|---|---|---|---|
| 1 | 24.7 | 4.9 | 9.0 | 12.2 | 2.01 | 0.16 | 0.53 | 0.30 | 1.77 | 0.28 | 0.29 |
| 2 | 25.0 | 5.2 | 8.4 | 11.9 | 2.02 | 0.17 | 0.49 | 0.30 | 1.63 | 0.26 | 0.28 |
| 3 | 22.0 | 8.5 | 9.3 | 11.0 | 1.81 | 0.29 | 0.55 | 0.28 | 1.96 | 0.16 | 0.19 |
| A | 24.1 | 7.9 | 9.4 | 12.2 | 2.04 | 0.28 | 0.57 | 0.32 | 1.78 | 0.38 | 0.39 |
| B | 22.5 | 7.0 | 8.1 | 14.7 | 1.90 | 0.24 | 0.49 | 0.38 | 1.29 | n.a. | 0.38 |
| C | 23.1 | 7.3 | 9.3 | 10.6 | 1.88 | 0.25 | 0.54 | 0.26 | 2.08 | n.a. | 0.38 |

[1] ratio of degree of substitution of acetyl groups/degree of substitution of succinoyl groups
[2] s23/s26 - 0.2*MS (hydroxypropyl) of the HPMC used as a starting material for HPMCAS
[3] Analyzed based on HPMCAS $DS_M$ = DS(methyl): degree of substitution with methoxyl groups; $MS_{HP}$ = MS(hydroxypropyl): molar substitution with hydroxypropoxyl groups
$DOS_{Ac}$: degree of substitution of acetyl groups; $DOS_s$: degree of substitution of succinoyl groups

TABLE 2

| HPMCAS of (Comparative) Example | Viscosity at 20° C. [mPa·s] [4] | Diameter [nm], Peak1 | $DOS_{Ac}/DOS_s$ [1] | s23/s26 - 0.2*MS (hydroxypropyl) [2] | s23/s26 - 0.2*MS (hydroxypropyl) [3] | Griseofulvin concentration [mg/L] at 180 min. | Phenytoin concentration [mg/L] at 180 min. |
|---|---|---|---|---|---|---|---|
| 1 | 4.1 | 56 | 1.77 | 0.28 | 0.29 | 460 | 220 |
| 2 | 4.4 | 21 | 1.63 | 0.26 | 0.28 | 490 | 215 |
| 3 | 4.4 | 42 | 1.96 | 0.16 | 0.19 | 990 | 260 |
| A | 5.5 | 8.6 | 1.78 | 0.38 | 0.39 | 560 | 210 |
| B | 3.0 | 5.0 | 1.29 | n.a. | 0.38 | 450 | 220 |

TABLE 2-continued

| HPMCAS of (Comparative) Example | Viscosity at 20° C. [mPa·s][4] | Diameter [nm], Peak1 | $DOS_{Ac}/DOS_s$ [1] | s23/s26 - 0.2*MS (hydroxy-propyl) [2] | s23/s26 - 0.2*MS (hydroxy-propyl) [3] | Griseofulvin concentration [mg/L] at 180 min. | Phenytoin concentration [mg/L] at 180 min. |
|---|---|---|---|---|---|---|---|
| C | 2.9 | 4.6 | 2.08 | n.a. | 0.38 | 720 | 270 |
| Control Run | — | — | — | — | — | 150 | 65 |

[1] ratio of degree of substitution of acetyl groups/degree of substitution of succinoyl groups
[2] s23/s26 - 0.2*MS (hydroxypropyl) of the HPMC used as a starting material for HPMCAS
[3] Analyzed based on HPMCAS
[4] measured as 2.0 wt % solution of the HPMCAS in 0.43 wt % aqueous NaOH at 20° C.

The invention claimed is:

1. An esterified hydroxypropyl methylcellulose comprising (i) aliphatic monovalent acyl groups or (ii) groups of the formula —C(O)—R—COOA wherein R is a divalent aliphatic or aromatic hydrocarbon group and A is hydrogen or a cation or (iii) a combination of aliphatic monovalent acyl groups and groups of the formula —C(O)—R—COOA, wherein the esterified hydroxypropyl methyl cellulose has anhydroglucose units joined by 1-4 linkages and has methyl groups and hydroxypropyl groups such that the esterified hydroxypropyl methylcellulose has an MS(hydroxypropyl) of 0.05 to 1.00, and hydroxyl groups of anhydroglucose units are substituted with methyl groups such that [s23/s26–0.2*MS(hydroxypropyl)] is from 0.13 to 0.33, wherein s23 is the molar fraction of anhydroglucose units wherein only the two hydroxyl groups in the 2- and 3-positions of the anhydroglucose unit are substituted with a methyl group and wherein s26 is the molar fraction of anhydroglucose units wherein only the two hydroxyl groups in the 2- and 6-positions of the anhydroglucose unit are substituted with a methyl group.

2. The esterified hydroxypropyl methylcellulose of claim 1 comprising (i) aliphatic monovalent acyl groups or (ii) groups of the formula —C(O)—R—COOH wherein R is a divalent aliphatic or aromatic hydrocarbon group or (iii) a combination of aliphatic monovalent acyl groups and groups of the formula —C(O)—R—COOH.

3. The esterified hydroxypropyl methylcellulose of claim 2 wherein the aliphatic monovalent acyl groups (i) are acetyl, propionyl or butyryl groups and wherein the groups (ii) of the formula —C(O)—R—COOH are —C(O)—CH$_2$—CH$_2$—COOH, —C(O)—CH=CH—COOH, or —C(O)—C$_6$H$_4$—COOH.

4. The esterified hydroxypropyl methylcellulose of claim 1 being a hydroxypropyl methylcellulose acetate succinate and having an [s23/s26–0.2*MS(hydroxypropyl)] of 0.13 to 0.31.

5. The esterified hydroxypropyl methylcellulose of claim 1 having a DS(methyl) of 1.2 to 2.2.

6. The esterified hydroxypropyl methylcellulose of claim 1 being hydroxypropyl methyl cellulose acetate succinate.

7. A process for preparing the esterified hydroxypropyl methylcellulose of claim 1 comprising the step of reacting a hydroxypropyl methylcellulose with (i) an aliphatic monocarboxylic acid anhydride or (ii) a dicarboxylic acid anhydride or (iii) a combination of an aliphatic monocarboxylic acid anhydride and a dicarboxylic acid anhydride, wherein the hydroxypropyl methylcellulose has anhydroglucose units joined by 1-4 linkages and has methyl groups and hydroxypropyl groups such that the hydroxypropyl methylcellulose has an MS (hydroxyalkyl) of 0.05 to 1.00, and hydroxyl groups of anhydroglucose units are substituted with methyl groups such that [s23/s26–0.2*MS(hydroxypropyl)] is from 0.13 to 0.31, wherein s23 is the molar fraction of anhydroglucose units wherein only the two hydroxyl groups in the 2- and 3-positions of the anhydroglucose unit are substituted with a methyl group and wherein s26 is the molar fraction of anhydroglucose units wherein only the two hydroxyl groups in the 2- and 6-positions of the anhydroglucose unit are substituted with a methyl group.

8. A liquid composition comprising an organic or aqueous diluent and at least one esterified hydroxypropyl methylcellulose of claim 1.

9. The liquid composition of claim 8 additionally comprising at least one active ingredient and optionally one or more adjuvants.

10. A process for coating a dosage form comprising the step of contacting the liquid composition of claim 8 with the dosage form.

11. A process for the manufacture of capsules comprising the step of contacting the liquid composition of claim 8 with dipping pins.

12. A solid dispersion of at least one active ingredient in at least one esterified hydroxypropyl methylcellulose of claim 1.

13. The solid dispersion of claim 12 wherein the solid dispersion has been formulated into tablets, pills, granules, pellets, caplets, microparticles, fillings of capsules, or into a paste, cream, suspension or slurry.

14. The esterified hydroxypropyl methylcellulose of claim 1 being a hydroxypropyl methylcellulose acetate succinate and having an [s23/s26–0.2*MS(hydroxypropyl)] of from 0.19 to 0.29.

15. The process of claim 7 wherein a hydroxypropyl methylcellulose having an [s23/s26–0.2*MS(hydroxypropyl)] of from 0.16 to 0.28 is esterified with acetic anhydride and succinic anhydride.

* * * * *